(12) United States Patent
Sasho et al.

(10) Patent No.: US 7,803,949 B2
(45) Date of Patent: Sep. 28, 2010

(54) PROCESS FOR PREPARATION OF WATER-SOLUBLE AZOLE PRODRUGS

(75) Inventors: Manabu Sasho, Tokyo (JP); Keizo Sato, Tsukuba (JP); Jun Niijima, Tsukuba (JP); Mamoru Miyazawa, Kamisu (JP); Shigeto Negi, Tsukuba (JP); Atsushi Kamada, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 167 days.

(21) Appl. No.: 12/097,244

(22) PCT Filed: Dec. 20, 2006

(86) PCT No.: PCT/JP2006/325352

§ 371 (c)(1),
(2), (4) Date: Jun. 12, 2008

(87) PCT Pub. No.: WO2007/072851

PCT Pub. Date: Jun. 28, 2007

(65) Prior Publication Data

US 2009/0192316 A1     Jul. 30, 2009

(30) Foreign Application Priority Data

Dec. 20, 2005  (JP) .............................. 2005-366862
Feb. 9, 2006   (JP) .............................. 2006-032913

(51) Int. Cl.
*C07F 9/06* (2006.01)
(52) U.S. Cl. ..................................... 548/112
(58) Field of Classification Search .................. 548/112
See application file for complete search history.

(56) References Cited

U.S. PATENT DOCUMENTS 6,362,172 B2 *   3/2002   Ueda et al. ..................... 514/85
6,448,401 B1 *   9/2002   Chen et al. ................... 544/243
2001/0041691 A1  11/2001  Ueda et al.
2002/0062028 A1   5/2002  Chen et al.
2006/0264406 A1* 11/2006  Gao et al. ..................... 514/85

FOREIGN PATENT DOCUMENTS

JP    2003-520235 A      7/2003
JP    2004-518640 A      6/2004
WO    WO 2006/118351 A1  11/2006

\* cited by examiner

*Primary Examiner*—Susannah Chung
(74) *Attorney, Agent, or Firm*—Birch, Stewart, Kolasch & Birch, LLP

(57) ABSTRACT

An object of the present invention is to provide a process, or the like, suitable for the industrialization of effective deprotection reaction without using a toxic solvent as well as to provide a process, or the like, for preparing a water-soluble azole prodrug effectively. The present invention provides a process for preparing a salt represented by Formula (I);

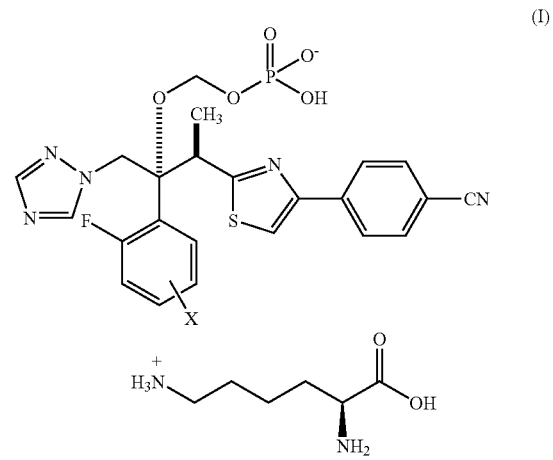

(wherein X represents a fluorine atom bonded at position 4 or position 5 of a phenyl group) comprising the steps of:

(a) carrying out a deprotection reaction of a compound represented by Formula (II);

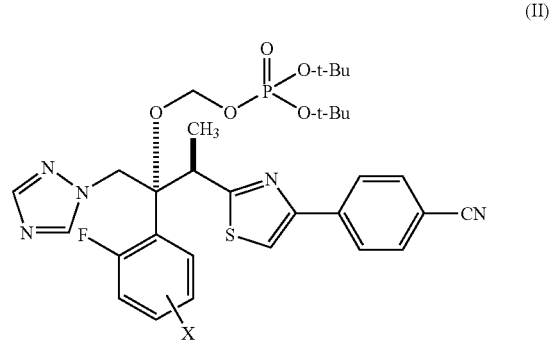

(wherein X represents a fluorine atom bonded at position 4 or position 5 of a phenyl group)
in the presence of a carbocation scavenger.

24 Claims, 2 Drawing Sheets

FIG.1

| ACID | CARBOCATION SCAVENGER | SOLVENT | REACTION TIME/ HOUR | DEPROTECTION/ % | AMIDE COMPOUND/ % |
|---|---|---|---|---|---|
| TRIFLUOROACETIC ACID (30 EQUIVALENTS) | NONE | DICHLOROMETHANE | 4 | 92.5 | 7.5 |
| | NONE | BUTYL ACETATE | 3 | 87.9 | 12.1 |
| | ANISOLE (14.1 EQUIVALENTS) | NONE | 3 | 95.3 | 4.7 |
| | THIOANISOLE (13.0 EQUIVALENTS) | NONE | 3 | 97.3 | 2.7 |
| | $CH_3CN$ (29.4 EQUIVALENTS) | NONE | 3 | 98.6 | 1.4 |
| | PHCN (15.0 EQUIVALENTS) | NONE | 1 | 97.1 | 2.9 |
| 8N HYDROCHLORIC ACID (30 EQUIVALENTS) | | METHANOL | 4 | 99.7 | 0.3 |

REACTION TEMPERATURE WAS 0°C

PROCESS FOR PREPARATION OF WATER-SOLUBLE AZOLE PRODRUGS

TECHNICAL FIELD

The present invention relates to an improvement of a process for preparation of a water-soluble prodrug. More specifically, the present invention relates to the process for preparation of the water-soluble azole prodrug having a phosphate group.

BACKGROUND ART

The compound represented by the following formula is known as one example of water-soluble prodrugs (for instance, refer to Patent Document 1 and Patent Document 2). This compound is a water-soluble azole prodrug useful for in the treatment of serious systemic fungal infection.

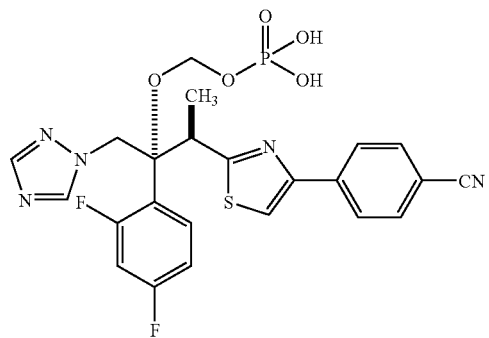

In addition, this water-soluble prodrug is also known to be preparable by the following scheme (refer to Patent Document 2 below).

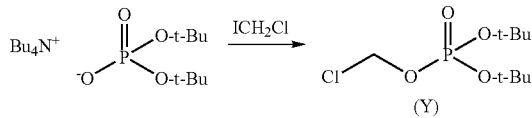

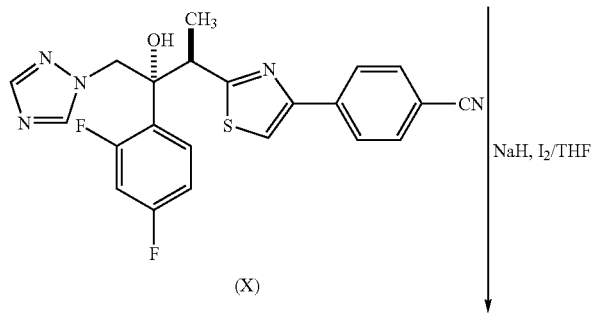

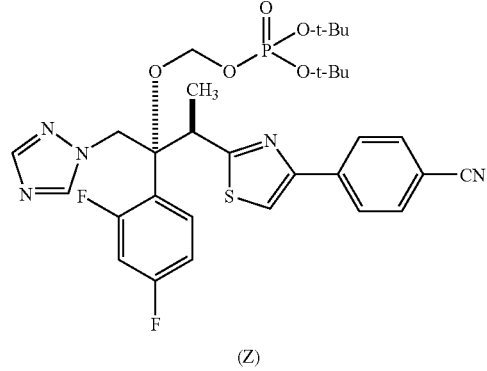

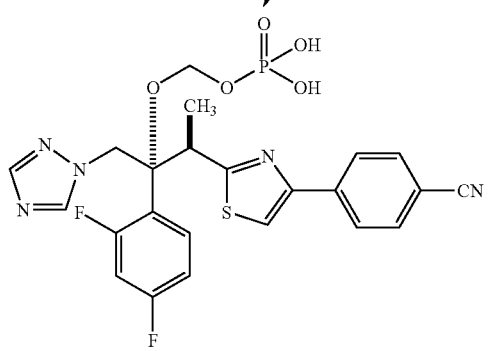

In the above formula, t-Bu represents tert-butyl, THF represents tetrahydrofuran and TFA represents trifluoroacetic acid. As illustrated in the above scheme, in order to prepare the water-soluble azole prodrugs, first, chloromethylphosphates (corresponding to Y in the above scheme) and active drug compounds (corresponding to X in the above scheme) having a hydroxyl group are reacted to obtain an intermediate compound Z, then, the intermediate compound Z is subjected to deprotection reaction to be converted into the water-soluble azole prodrugs. Introducing in this way a phosphonooxymethyl moiety into a hydroxyl group-containing drug is known as a process for preparing the water-soluble prodrugs of the hydroxyl group-containing drug. Note that the term "prodrug" means a derivative of a drug compound, which reverts in vivo to the original drug compound (hereinafter sometimes referred to as "parent compound"); water-soluble prodrug formulation of active ingredients is often the subject of research and development.

Then, when the deprotection reaction of the above intermediate compound Z is followed by sodium salt formation, the reaction yield from these two steps has been reported to be approximately 12% (following scheme: for example, refer to Patent Document 1). Note that, in the following formula, t-Bu represents tert-butyl.

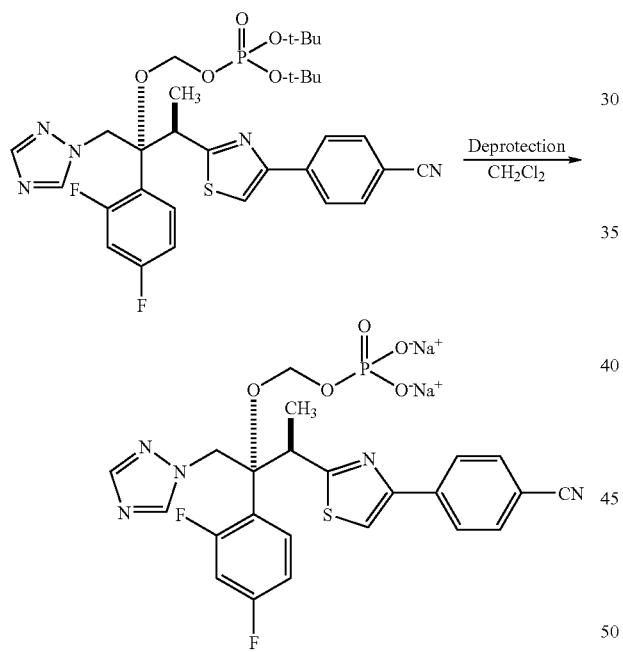

However, since the intermediate compound Z deprotection reactions disclosed in Patent Document 1 and Patent Document 2 use a halogen-based solvent such as methylene chloride, industrialization thereof would place a large burden on the environment, accompanied by the complexity of waste liquid treatment.

In addition, as described earlier, since the reaction yield when deprotection reaction is followed by sodium salt formation is 12%, with this reaction yield, the reaction cannot be called effective from the point of view of industrial preparation, and is extremely inadequate for large amount syntheses at an industrial scale. Therefore, additional improvements are sought regarding the deprotection reaction of the above-mentioned intermediate compound Z from the point of view of industrial preparation.

Meanwhile, as a preferred mode of water-soluble azole prodrug, a pharmacologically acceptable salt of the prodrug is disclosed in the above Patent Document 1. In addition, in Patent Document 1, water-solubility is reported to be better than that of the parent compound, by turning the prodrug into a salt. Specifically, a dilysine salt and a tert-butyl amine salt of water-soluble azole prodrugs are disclosed in Patent Document 1; however, improvement of physical properties of the salt per se is sought, in addition to solubility in water.

[Patent Document 1] Published Japanese Translation of a PCT Application No. 2003-520235 (International Publication No. WO01/52852)

[Patent Document 2] Published Japanese Translation of a PCT Application No. 2004-518640 (International Publication No. WO02/42283)

DISCLOSURE OF THE INVENTION

Problems to be Solved by the Invention

An object of the present invention is to provide a process for preparation, or the like, suitable for the industrialization of the deprotection reaction in the above intermediate compound Z without using a toxic solvent, as well as to provide a process, or the like, for preparing effectively a high quality water-soluble azole prodrug.

Thus, in view of the above situation, the present inventors carried out earnest studies on the deprotection reaction of tert-butyl phosphate derivative, which is the intermediate compound Z, and as a result, found that the by-production of amide compound in the process of deprotection could be suppressed by carrying out the deprotection reaction in the presence of a carbocation scavenger, allowing the deprotection reaction yield to be brought to approximately 85% or greater, and that this deprotection reaction was suitable for the industrial process for preparation, thereby leading to completion of the present invention.

That is to say, the present invention provides:

[1] a process for preparing a salt represented by Formula (I);

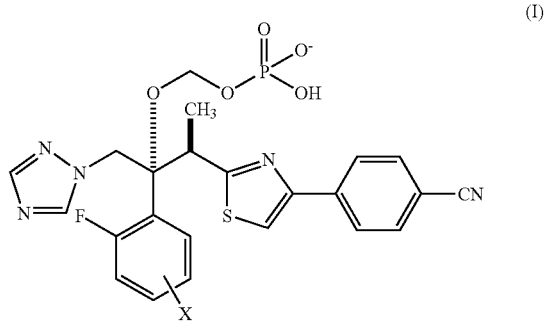

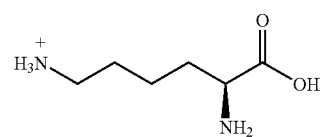

(wherein X represents a fluorine atom bonded at position 4 or position 5 of a phenyl group) comprising the steps of:

(a) carrying out a deprotection reaction of a compound represented by Formula (II);

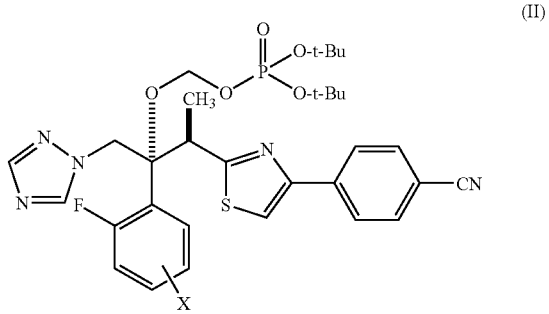

(wherein X represents a fluorine atom bonded at position 4 or position 5 of a phenyl group)

in the presence of a first organic acid and/or a carbocation scavenger to produce a compound represented by Formula (III);

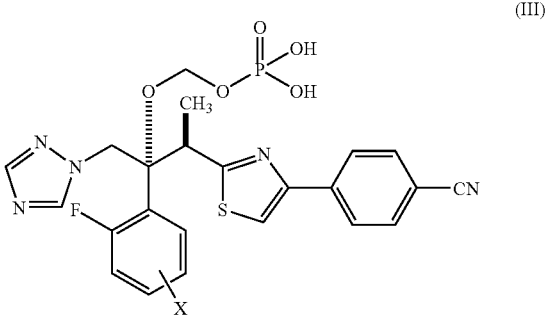

(wherein X represents a fluorine atom bonded at position 4 or position 5 of a phenyl group); and (b) reacting the compound represented by Formula (III) with lysine in the presence of water, an organic solvent and an acid (with the proviso that the carbocation scavenger is always present when the first organic acid is used),

[2] the process according to item [1], wherein the first organic acid is selected from the group consisting of trifluoroacetic acid, methanesulfonic acid, trifluoromethane sulfonic acid, benzene sulfonic acid and toluene sulfonic acid,

[3] the process according to item [1] or [2], wherein the carbocation scavenger is selected from the group consisting of inorganic acid, C1-C6 alkoxybenzene which may have a substituent, C1-C8 alkylthiobenzene which may have a substituent, nitrile compound and mixtures thereof,

[4] the process according to item [3], wherein the inorganic acid is selected from the group consisting of hydrofluoric acid, hydrochloric acid, hydrobromic acid, hydroiodic acid, nitric acid, sulfuric acid and phosphoric acid,

[5] the process according to item [3], wherein the C1-C6 alkoxybenzene which may have a substituent is anisole or m-methoxy anisole,

[6] the process according to item [3], wherein the C1-C6 alkylthiobenzene is thioanisole,

[7] the process according to item [3], wherein the nitrile compound is selected from the group consisting of acetonitrile, propiononitrile and benzonitrile,

[8] the process according to any one of items [1] to [7], wherein a solvent selected from the group consisting of ester solvent, ether solvent, alcohol solvent and mixed solvents thereof is used when the first organic acid and the carbocation scavenger is used in said step (a),

[9] the process according to any one of items [1] to [7], wherein a solvent selected from the group consisting of ether solvent, alcohol solvent and mixed solvents thereof is used when only the carbocation scavenger is used in said step (a),

[10] the process according to item [8], wherein the ester solvent is selected from the group consisting of ethyl acetate, butyl acetate and mixed solvents thereof,

[11] the process according to item [8] or [9], wherein the ether solvent is selected from the group consisting of diethyl ether, dimethoxy ethane, methyl tert-butyl ether, tetrahydrofuran and mixed solvents thereof,

[12] the process according to item [8] or [9], wherein the alcohol solvent is selected from the group consisting of methanol, ethanol, 1-propanol, 2-propanol and mixed solvents thereof,

[13] the process according to item [9], wherein the carbocation scavenger is an inorganic acid,

[14] the process according to any one of items [1] to [13], wherein the step (a) is carried out at a temperature of from −20° C. to 10° C.,

[15] the process according to any one of items [1] to [14], wherein the organic solvent is an organic solvent miscible with water, and the acid is a second organic acid,

[16] the process according to item [15], wherein the organic solvent miscible with water is selected from the group consisting of methanol, ethanol, 1-propanol, 2-propanol and mixed solvents thereof,

[17] the process according to item [15] or [16], wherein the organic solvent miscible with water is ethanol,

[18] the process according to any one of items [15] to [17], wherein the second organic acid is selected from the group consisting of acetic acid, propionic acid and butyric acid,

[19] the process according to any one of items [1] to [18], further comprising the steps of:

(c) carrying out crystallization in the organic solvent miscible with water so as to produce a solvate of the salt represented by the Formula (I),

[20] the process according to item [19], wherein the solvate is a solvate represented by Formula (IV);

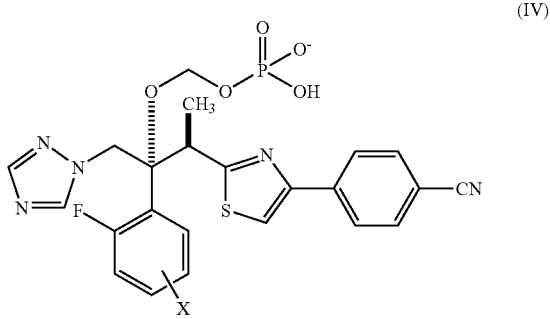

-continued

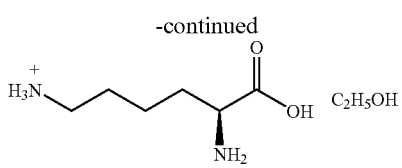

(wherein X represents a fluorine atom bonded at position 4 or position 5 of a phenyl group), and the organic solvent miscible with water is ethanol,

[21] the process according to any one of items [1] to [20], wherein the compound represented by the Formula (II) is obtained by reacting a compound represented by Formula (V);

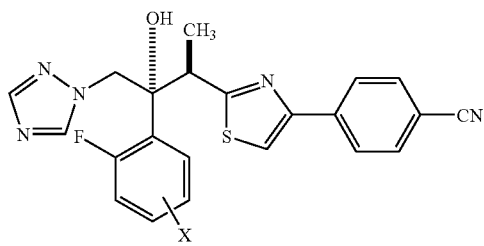

(wherein X represents a fluorine atom bonded at position 4 or position 5 of a phenyl group), with a compound represented by Formula (VI);

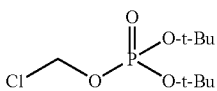

in a solvent containing a base.

Note that in Formula (VI), t-Bu represents tert-butyl.

Advantageous Effects of the Invention

According to the process for the preparation according to the present invention, an effective deprotection reaction of a tert-butyl phosphate intermediate compound can be realized without using halogen-based solvents, which can be applied to the preparation of high quality water-soluble azole prodrugs at an industrial scale.

BEST MODE FOR CARRYING OUT THE INVENTION

Hereinafter, the meanings of the symbols and terms described in the present specification, embodiments of the present invention and the like, will be indicated to describe the present invention in detail. The following embodiments are exemplary to explain the present invention, and the present invention is not intended to be limited to these embodiments only. The present invention may be carried out in various modes as long as they do not depart from the gist thereof.

The term "carbocation scavenger" used in the present invention refers to a compound that traps tert-butyl carbocation or isobutene, which is the rearrangement reaction product thereof, generated during the deprotection reaction of tert-butoxy group. Specific examples of the carbocation scavengers used in the present invention may include, inorganic acids, C1-C6 alkoxybenzene which may have a substituent, C1-C6 alkylthiobenzene which may have a substituent, nitrile compounds and the like. These carbocation scavengers may be used alone, or two or more species may be used in combination.

The term "C1-C6 alkyl group" in "C1-C6 alkylthiobenzene which may have a substituent" used in the present invention refers to a linear or branched alkyl group having 1 to 6 carbons, which is a monovalent group derived by removing any hydrogen atom from an aliphatic hydrocarbon having 1 to 6 carbons. Specific examples of "C1-C6 alkyl group" may include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group and the like, preferably, a methyl group, an ethyl group, a n-propyl group, an isopropyl group, a n-butyl group, an isobutyl group, a sec-butyl group, a tert-butyl group and the like.

The term "which may have substituent" in the term "C1-C6 alkoxybenzene which may have a substituent" and in the term "C1-C6 alkylthiobenzene which may have a substituent" which are used in the present invention means that one to a plurality of substituents may be present in an arbitrary combination at a substitutable site. Specific examples of the substituent may include; (1) a halogen atom (for instance, a fluorine atom, a chlorine atom, a bromine atom, an iodide atom and the like); (2) a hydroxyl group; (3) a cyano group; (4) a nitro group; (5) a carboxyl group; (6) an amino group and the like.

The term "C1-C6 alkoxy" in the term "C1-C6 alkoxybenzene which may have substituent" used in the present invention refers to a group having an oxygen atom bonded to an end of the "C1-C6 alkyl group" defined above. Examples thereof may include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methyl butoxy group, a 2-methyl butoxy group, a 1,1-dimethylpropoxy group, a 1,2-dimethylpropoxy group, a n-hexyloxy group, an isohexyloxy group, a 1-methyl pentyloxy group, a 2-methyl pentyloxy group, a 3-methyl pentyloxy group, a 1,1-dimethyl butoxy group, a 1,2-dimethyl butoxy group, a 2,2-dimethyl butoxy group, a 1,3-dimethyl butoxy group, a 2,3-dimethyl butoxy group, a 3,3-dimethyl butoxy group, a 1-ethyl butoxy group, a 2-ethyl butoxy group, a 1,1,2-trimethylpropoxy group, a 1,2,2-trimethylpropoxy group, a 1-ethyl-1-methylpropoxy group, a 1-ethyl-2-methylpropoxy group and the like, preferably, a methoxy group, an ethoxy group, a n-propoxy group, an isopropoxy group, a n-butoxy group, an isobutoxy group, a sec-butoxy group, a tert-butoxy group and the like. Specific examples "C1-C6 alkoxybenzene which may have a substituent" used in the present invention may include anisole, o-, m-, p-methoxy anisole, o-, m-, p-ethoxy anisole, 1,3,5-dimethoxy benzene, 1,3,5-ethoxy benzene and the like, preferably anisole and o-, m-, p-methoxy anisole, and more preferably anisole and m-methoxy anisole.

The term "C1-C6 alkylthio" in the term "C1-C6 alkylthiobenzene which may have a substituent" used in the present invention refers to a group having a sulfur atom bonded to an end of the "C1-C6 alkyl group" defined above. Examples thereof may include a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a sec-pentylthio group, a neopentylthio group, a 1-methylbutylthio group, a 2-methylbutylthio group, a 1,1-dimethylpropylthio group, a 1,2-dimethylpropylthio group, a n-hexylthio group, an isohexylthio group, a 1-methyl pentylthio group, a 2-methyl pentylthio group, a 3-methyl pentylthio group, a 1,1-dimethylbutylthio group, a 1,2-dimethylbutylthio group, a 2,2-dimethylbutylthio group, a 1,3-dimethylbutylthio group, a 2,3-dimethylbutylthio group, a 3,3-dimethylbutylthio group, a 1-ethylbutylthio group, a 2-ethylbutylthio group, a 1,1,2-trimethylpropylthio group, a 1,2,2-trimethylpropylthio group, a 1-ethyl-1-methylpropylthio group, a 1-ethyl-2-methylpropylthio group and the like, preferably a methylthio group, an ethylthio group, a n-propylthio group, an isopropylthio group, a n-butylthio group, an isobutylthio group, a sec-butylthio group, a tert-butylthio group and the like. Note that the term "may have a substituent" in the term "C1-C6 alkylthiobenzene which may have a substituent" used in the present invention has the same meaning as defined above. Specific examples of "C1-C6 alkylthiobenzene which may have a substituent" used in the present invention may include thioanisole, o-, m-, p-methylthioanisole, o-, m-, p-ethylthioanisole, 1,3,5-trimethylthiobenzene, 1,3,5-triethylthiobenzene and the like, preferably thioanisole and o-, m-, p-methylthioanisole, and more preferably thioanisole.

The term "nitrile compound" used in the present invention refers to a compound having a —CN group. Specific examples of "nitrile compound" used in the present invention may include acetonitrile, propiononitrile, benzonitrile which may have s substituent and the like, preferably acetonitrile, propiononitrile or benzonitrile, and more preferably acetonitrile and benzonitrile.

The term "first organic acid" used in the present invention refers to an organic compound, which is an acid used during a deprotection reaction, exhibiting acidity. Meanwhile, the term "second organic acid" used in the present invention refers to an organic compound, which is an acid used during formation of a salt after deprotection reaction of the phosphate group, exhibiting acidity.

Hereinafter, the effects of the carbocation scavenger in the deprotection reaction in the present invention will be described in detail. As disclosed in the above-mentioned Published Japanese Translation of PCT Application No. 2003-520235, the reaction yield of the following reaction has been reported to be approximately 12%.

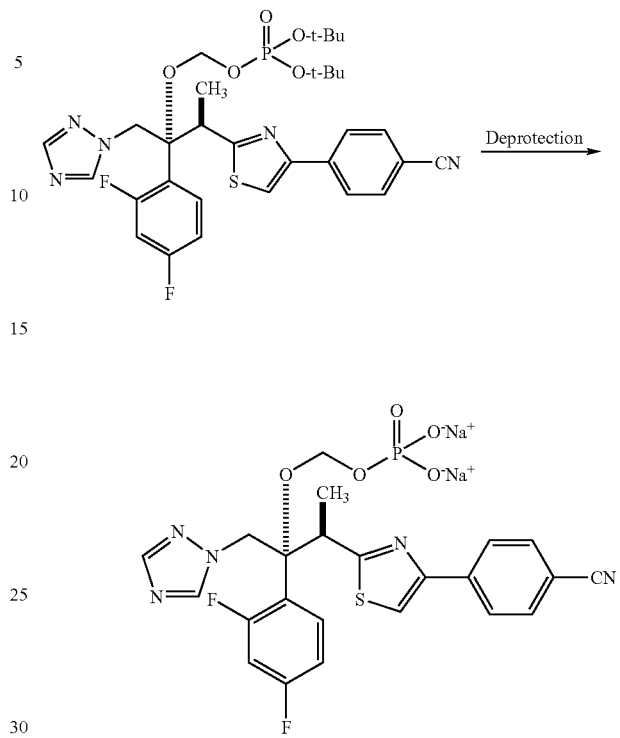

In view of the above, when improvement of such a low yield deprotection reaction was examined, it is discovered in the present invention that if the above deprotection reaction is carried out in the presence of the carbocation scavenger, the reaction yield of this deprotection reaction is improved dramatically.

In addition, since the deprotection reaction according to the present invention uses ester solvents, ether solvents or alcohol solvents, and carbocation scavengers as a solvent not containing halogen atom, without using halogen-based on solvents, it puts less burden on the environment and is less likely to be accompanied by the complexity of waste liquid treatment as compared to when the halogen-based solvents are used, allowing the deprotection reaction according to the present invention to be applied as an industrial preparation.

In the following explanation, a process for preparing a water-soluble azole prodrug will be described, including the deprotection reaction according to the present invention. The following scheme indicates the process for preparing the water-soluble azole prodrug including the deprotection reaction according to the present invention.

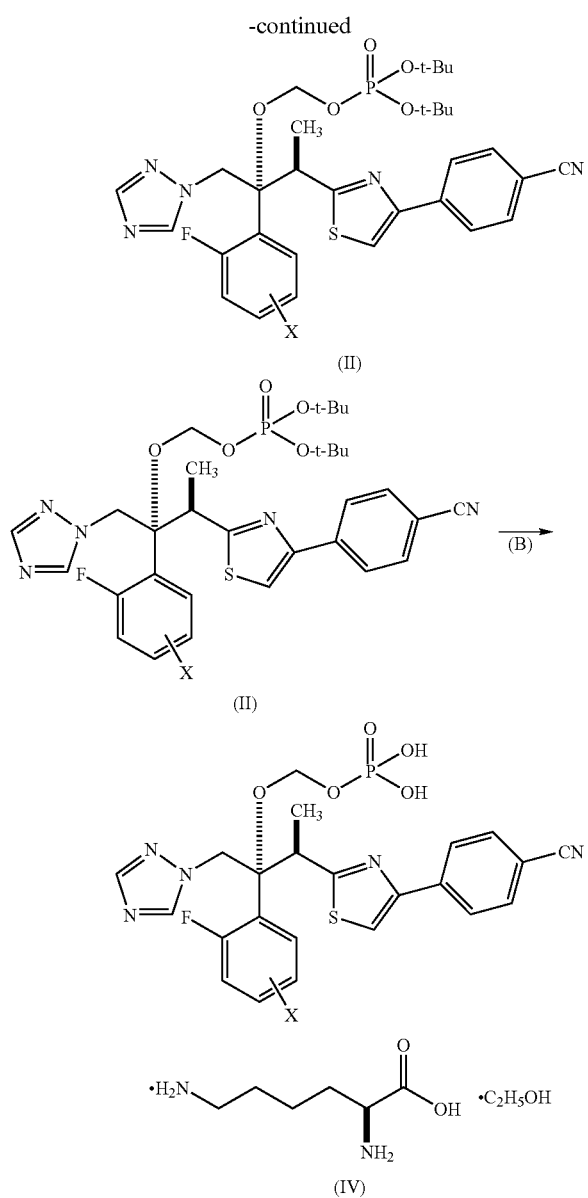

(in the above scheme, X represents a fluorine atom bonded at position 4 or position 5 of the phenyl group.)

As shown in the above scheme, the process for the preparation of the water-soluble azole prodrug according to the present invention comprises introducing a tert-butoxy phosphonooxymethyl moiety into a hydroxyl group-containing drug compound by Step (A) and the deprotection reaction and salt formation by Step (B).

With respect to Step (A)

Step (A) is a step in which the compound represented by Formula (II) is prepared using the compound represented by Formula (V) as the parent compound and the chloromethylphosphate compound represented by Formula (VI). The compound represented by Formula (V) will hereinafter simply be abbreviated to be Compound (V), the compound represented by Formula (VI) will hereinafter simply be abbreviated to be Compound (VI) etc. (similarly for compounds represented by other formulae). Examples of Compound (V) applicable to the deprotection reaction according to the present invention may include, but are not limited to, triazole-based antifungal compounds having a hydroxyl group. Specific examples may include compounds having the following structural formula, and the like.

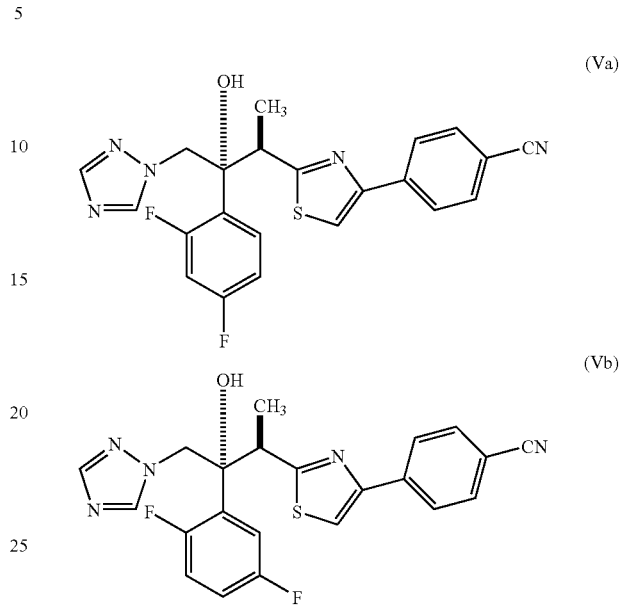

Herein, Compound (Va) is disclosed in U.S. Pat. No. 5,648,372, and can be prepared according to the description disclosed in the patent. On the other hand, Compound (Vb) is disclosed in U.S. Pat. No. 6,300,353, and can be prepared according to the description disclosed in this patent.

For di-tert-butyl chloromethylphosphate, which is Compound (VI), commercially available product may be used as-is, or it can also be prepared from the commercially available products according to the reaction scheme shown below.

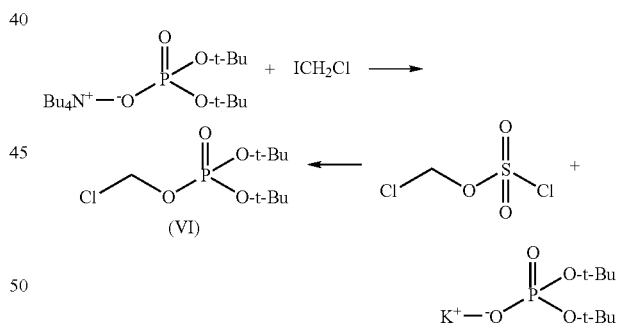

As shown above, Compound (VI) can be prepared by the process for the preparation from the commercially available product, tetrabutylammonium di-tert-butylphosphate and chloroiodomethane, the process for the preparation from the commercially available product, potassium di-tert-butyl phosphate and chloromethyl chlorosulfonate, and the like.

Describing Step (A) in detail, this step is a step in which Compound (V), which is an antifungal parent compound having a hydroxyl group is converted into phosphate (II) by carrying out o-alkylation using Compound (VI) in the presence of a base. In particular, when iodide or an iodide ion source is added in this step, the yield of o-alkylation is improved dramatically. Specific examples of base used in the present step may include, but are not limited to, sodium hydride, potassium hydride, sodium amide, sodium tert-butoxide, sodium bis(trimethylsilyl)amide, potassium bis(trimethylsilyl)amide or combinations thereof. Specific examples of iodide ion source used in the present step may include, but are not limited to, iodide, sodium hydride, lithium iodide, sodium iodide, tetrabutylammonium iodide and the like. At least 1 equivalent to 1.5 equivalents of Compound (VI) are used based on Compound (V), 0.1 equivalents to 3 equivalents of iodide ion source are used based on Compound (V), and 1 to 4 equivalents of the base are used based on Compound (V) of base. Specific examples of solvents used in the present step may include, although there is no particular limitation as long as they dissolve the starting materials to some extent without inhibiting the reaction, dimethoxyethane, tetrahydrofuran, methyl tert-butyl ether, diethyl ether, dimethyl acetamide and the like.

The reaction temperature in the present Step (A) is not limited in particular, and is generally from −5 to 50° C., preferably from 0 to 40° C., and more preferably from 10 to 35° C.; the reaction time is not limited in particular, and is generally from 1 to 36 hours, preferably from 2 to 24 hours, and more preferably from 3 to 20 hours.

Compound (II) obtained in this way may be used as-is in the next Step (B); it can also be extracted with ether solvents after reaction is completed, and tertiary amine may be added in order to stabilize Compound (II), as necessary. Specific examples of the ether solvents used in the extraction may include tetrahydrofuran, methyl tert-butyl ether, diethyl ether and the like. In addition, specific examples of the tertiary amine used in the stabilization may include, but are not limited to, trialkylamine or N-alkylmorpholine and the like, preferably triethylamine, N,N-diisopropylethylamine and N-methylmorpholine, and more preferably N-methyl morpholine.

With Respect to Step (B)

Step (B) is a step in which Compound (II) is subjected to a deprotection reaction while at the same time a salt of the water-soluble azole prodrug, for example, Compound (IV), is prepared. In more detail, this Step (B) comprises the step of carrying out the deprotection reaction in the presence of the carbocation scavenger as described above, the step of carrying out a predetermined post-processing after this deprotection reaction without taking out Compound (III) per se, which is a reaction product, the step of forming the desired salt, and the step of crystallizing a solvate containing the salt.

The step of carrying out the deprotection reaction according to the present invention is broadly divided into two cases, in which one is carried out in the presence of the first organic acid and carbocation scavenger used in the deprotection reaction (hereinafter simply referred to as "first aspect of the deprotection reaction according to the present invention") and the other is carried out in the presence of only the carbocation scavenger (hereinafter simply referred to as "second aspect of the deprotection reaction according to the present invention"). Herein, the case of carrying out the deprotection reaction in the presence of only the carbocation scavenger, that is to say, the case of the second mode of the deprotection reaction according to the present invention, is a case in which an inorganic acid is used, and since the inorganic not only is used in the deprotection reaction but also plays the role of the carbocation scavenger, a decrease in the costs can be realized for industrial preparation on the point that other acids such as the aforementioned first organic acid are unnecessary.

In the first aspect of the deprotection reaction according to the present invention, this reaction is carried out in the presence of the first organic acid and the carbocation scavenger. The first organic acid used in the first aspect of the deprotection reaction according to the present invention, is an acid used in deprotection reaction. Specific examples of the first organic acid used in the present invention may include trifluoroacetic acid, methanesulfonic acid, trifluoromethanesulfonic acid, benzenesulfonic acid, toluenesulfonic acid and the like, preferably trifluoroacetic acid, trifluoromethanesulfonic acid and toluene sulfonic acid, and more preferably trifluoroacetic acid.

Specific examples of the carbocation scavenger used in the first aspect of deprotection reaction according to the present invention may include C1-C6 alkoxybenzene which may have a substituent, C1-C6 alkylthiobenzene which may have a substituent, nitrile compounds and combinations thereof, preferably anisole, m-methoxyanisole, thioanisole, acetonitrile, propiononitrile, benzonitrile and combinations thereof, and the like. Preferably, at least approximately 30 equivalents of the first organic acid is used based on Compound (II) and at least 5 equivalents of the carbocation scavenger is used based on Compound (II).

Specific examples of the solvents used in the first aspect of the deprotection reaction according to the present invention may include, although there is no particular limitation as long as they dissolve the starting materials to some extent without inhibiting the reaction, ester solvents, ether solvents, alcohol solvents, and the like, preferably, ethyl acetate, butyl acetate, diethyl ether, dimethoxymethane, methyl tert-butyl ether, tetrahydrofuran, methanol, ethanol, 1-propanol, 2-propanol, and the like, and more preferably, butyl acetate, dimethoxy ethane, methyl tert-butyl ether and methanol. Note that, in the case of the first aspect of the deprotection reaction according to the present invention, when the carbocation scavenger used is a solution, the carbocation scavenger per se can be also used as the solvent.

In the second aspect of the deprotection reaction according to the present invention, the deprotection reaction is carried out in the presence of only the carbocation scavenger. In this case, the carbocation scavenger is an inorganic acid. The term "inorganic acid" as carbocation scavenger used in the present invention, refers to an acid containing a nonmetal, such as, fluorine, chlorine, bromine, iodide, sulfur, nitrogen and phosphorus. Specific examples of inorganic acid used in the present invention may include hydrochloric acid, perchloric acid, hypochlorous acid, nitric acid, sulfuric acid, phosphoric acid, hydrofluoric acid, hydrobromic acid, hydroiodic acid and the like, preferably hydrochloric acid, hydrofluoric acid, hydrobromic acid, hydroiodic acid, nitric acid, sulfuric acid and phosphoric acid, and more preferably hydrochloric acid. Preferably, 20 to 40 equivalents of the carbocation scavenger in the second aspect of the deprotection reaction according to the present invention is used based on Compound (II), and, particularly preferably, approximately 30 equivalents of the carbocation scavenger are used. Specific examples of solvent used in the second aspect of the deprotection reaction according to the present invention may include, although there is no particular limitation as long as they dissolve the starting materials to some extent without inhibiting the reaction, ether solvents, alcohol solvents and the like, preferably diethyl ether, dimethoxy methane, methyl tert-butyl ether, tetrahydrofuran, methanol, ethanol, 1-propanol, 2-propanol and the like, and more preferably dimethoxy methane and ethanol.

The reaction temperature of the deprotection reaction in the first and second aspects of the present invention is not limited in particular, and is generally from −20 to 10° C., preferably from −10 to 8° C., and more preferably from −5 to 5° C.; the reaction time is from 0.1 to 10 hours, preferably from 0.2 to 8 hours, and more preferably from 0.5 to 6 hours.

With Respect to Post-processing Step

As described above, since the deprotection reaction in the first and second aspects employ acids, post-processing by neutralization using bases is preferably carried out while transferring the used acids to an aqueous layer. Specific examples of the base may include dipotassium hydrogenphosphate, disodium hydrogenphosphate and the like can.

With Respect to the Salt Generation to Crystallization Steps

Next, the salt represented by Formula (I) is produced without taking out Compound (III). Note that the salt may also be produced once Compound (II) has been taken out. In addition, a solvate of salt, such as represented by Formula (IV), can also be produced, as necessary.

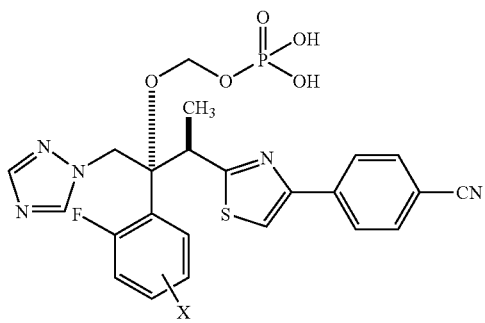
(III)

(in the above chemical formula, X represents a fluorine atom bonded at position 4 or position 5 of the phenyl group.)

The formation of the salt is carried out by reacting Compound (III) with lysine in the presence of water, an organic solvent and an acid, producing a mono lysine salt of Compound (III) (salt represented by Formula (I)).

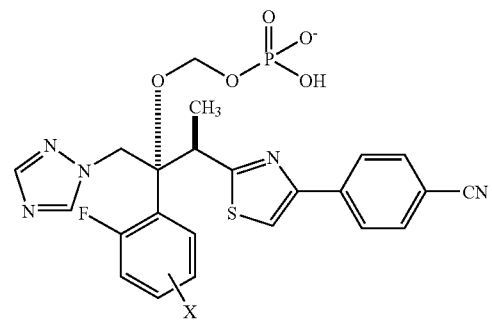
(I)

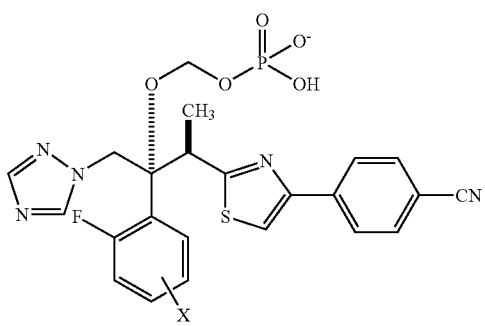
(IV)

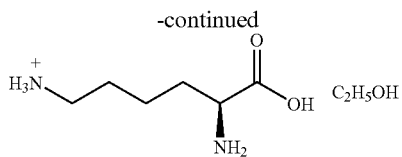
-continued (in the above chemical formula, X represents a fluorine atom bonded at position 4 or position 5 of the phenyl group.)

Here, the organic solvent is preferably an organic solvent miscible with water. Specific examples of organic solvent may include, although there is no particular limitation as long as they dissolve the starting materials to some extent without inhibiting the reaction, methanol, ethanol, 1-propanol, 2-propanol and the like, preferably methanol and ethanol, and more preferably ethanol. The acid is a second organic acid different from the first organic acid used in the deprotection reaction. Examples of the second organic acid may include acetic acid, propionic acid, butyric acid and the like, and preferably acetic acid. When converting into a lysine salt, for the lysine used, preferably at least 1 to 3 equivalents of the second organic acid are used based on Compound (III), and an aqueous solution of lysine salt is used. The temperature when converting into a salt is not limited in particular, which is from room temperature to 40° C., and preferably from room temperature to 35° C.

In more detail, in order to produce effectively a solvated salt of Compound (III) using an aqueous solution of dissolved lysine, the following procedure is performed preferably. First, Compound (III) is extracted using an aqueous solution containing an alkaline metal salt. Examples of the alkaline metal salts in this case may include, but are not limited to, potassium phosphate, sodium phosphate and the like. Thereafter, the aqueous solution containing the alkaline metal chlorinated Compound (II) is neutralized momentarily with an acid, as necessary, while further adjusting a pH of this aqueous solution to 3 or less, preferably to 2.5 or less, and more preferably to 2.2 or less, Compound (III) is extracted with an organic solvent such as butyl acetate, then, treated with an aqueous solution containing lysine, allowing an aqueous solution containing the lysine chlorinated Compound (III) to be obtained.

Thereafter, the above second organic acid is added to the aqueous solution containing the lysine chlorinated Compound (III), the pH of the aqueous solution is adjusted to 6 or less, preferably to 5.5 or less, and more preferably to 5.0 or less, then, when the above organic solvent miscible with water is added, a monolysine salt solvated by the organic solvent is produced efficiently. Acetic acid is particularly preferred as the second organic acid mentioned above. In addition, ethanol is preferred as the organic solvent mentioned above, and the compound represented by Formula (IV) is prepared as the solvate. A seed crystal may be added for crystallization as a solvate. Specifically, after ethanol has been added, the temperature of the reaction solution is raised to 35 to 60° C., and stirring is carried out for 1 hour to 8 hours, and preferably for 2 hours to 7 hours. Thereafter, the temperature of the reaction solution is cooled to 5 to 30° C., and preferably to 22 to 28° C., stirring is carried out for at least 17 hours or longer, and preferably for 17 hours to 65 hours, and then, the produced crystal is recovered by filtration. In this way, from Compound (II), which is the starting material, via the highly efficient deprotection reaction according to the present invention, Compound (IV) can be prepared and isolated.

EXAMPLES

Hereinafter, the present invention will be described more specifically by showing examples and the like, however, these descriptions are illustrative and the present invention is not limited by these in any case,

Example 1

Di-tert-butyl-{[(1R,2R)-2-(4-cyanophenyl)-1,3-thiazol-2-yl]-1-(2,4-difluorophenyl)-1-(1H-1,2,4-triazol-1-ylmethyl) propyl}-oxy]methyl phosphate

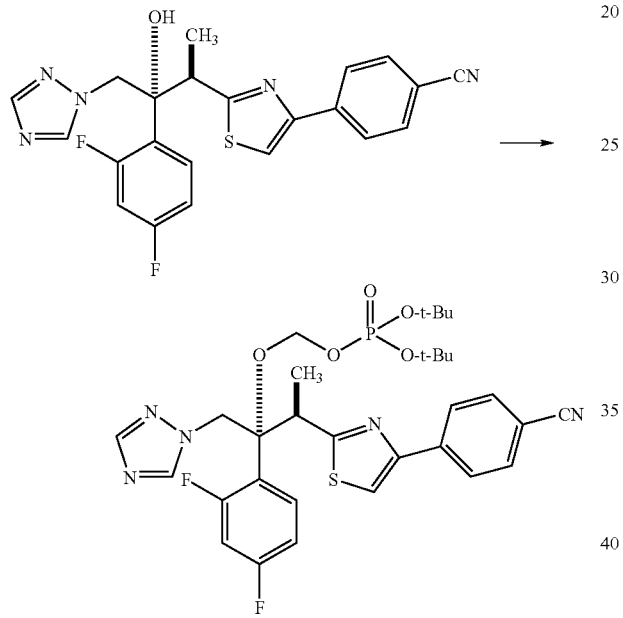

In a 2 L 4-neck flask, 17.77 g of 62% sodium hydride (0.46 mot) was weighed and tetrahydrofuran (113 mL) was added under a nitrogen atmosphere. The bath temperature was set to −5° C. and stirring was carried out for 12 minutes, then, a solution of 20.44 g of iodide (0.080 mol) dissolved in tetrahydrofuran (113 mL) was added dropwise thereto. The bath temperature was set to 20° C. and stirring was carried out for 78 minutes, then, the bath temperature was set again to −5° C. and stirring was carried out for 65 minutes. A solution of 70.5 g 4-{2-[(1R,2R)-2-(2,4-difluorophenyl)-2-hydroxy-1-methyl-3-(H-1,2,4-triazol-1-yl)propyl]-1,3-thiazol-4-yl} benzonitrile (0.16 mol) dissolved in tetrahydrofuran (289 mL) was added dropwise over 16 minutes, followed by stirring for 48 minutes at a bath temperature of −5° C. A solution containing 64.36 g of di-tert-butyl chloromethyl phosphate in tetrahydrofuran (7 mL) was added thereto followed by stirring overnight with the bath temperature set to 20° C. The bath temperature was set to −5° C., and after cooling, 3.2 g of phosphoric acid contained in tert-butyl methyl ether (529 mL) was added thereto dropwise over 24 minutes. After stirring for 90 minutes, 352 mL of water was added thereto, and a further 352 mL of water was added to carry out liquid separation. Next, after sequentially washing with 704 mL of an aqueous solution of 2% NaOH, sodium chloride water and water, 3.20 g of N-methyl morpholine was added to the separated organic layer and concentrated at a bath temperature of 30° C. under a reduced pressure to obtain 196 g of the title compound (containing net 100 g).

Using the compound of Example 1 obtained in this way, deprotection reaction in the presence of carbocation scavenger was examined. Specifically, with respect to the compound of Example 1, 30 equivalents of trifluoroacetic acid was added, and a deprotection reaction was carried out under conditions where various carbocation scavengers were present. The deprotection reaction was followed up by high performance liquid chromatography under the conditions indicated below:

Phenomenex Luna 3 μm C8(2) 4.6×150 mm.I.D.

Mobile phase: $CH_3CN:H_2O$:ammonium acetate=300:700:2.3 (v/v/w)

UV detection wavelength: 282 nm; flow rate: 1.0 mL/min

FIG. 1 shows the results obtained by the first aspect of the deprotection reaction according to the present invention. Note that the deprotected compound indicated in FIG. 1 refers to the compound represented by the following Formula (VII (a)), and the amide compound refers to the compound represented by the following Formula (VII (b)).

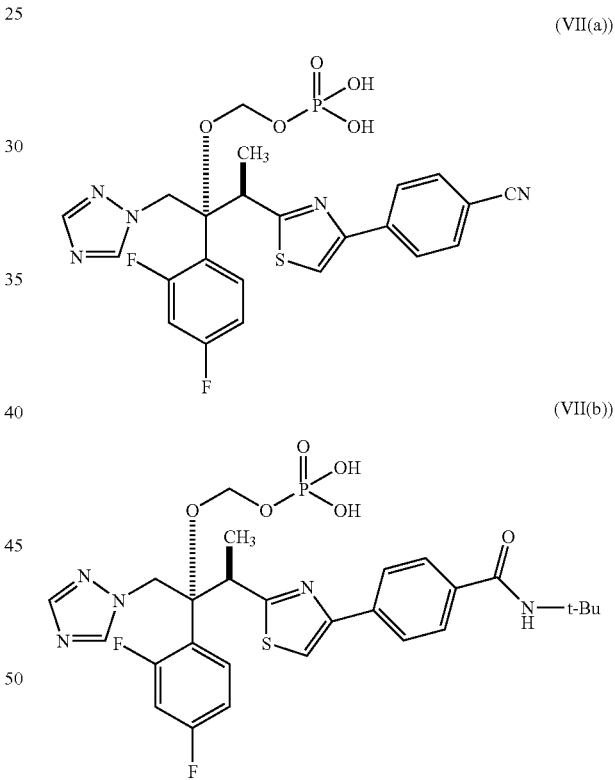

Amide Compound (Compound (VII (b)) NMR:

$^1$H-NMR (CD$_3$OD,400 MHz) δ: 1.31 (d,J=7 Hz,3H), 1.38 (s,9H), 3.96 (q,J=7 Hz,1H), 5.15 (dd,J=15,15 Hz,2H), 5.42 (dd,J=10,9 Hz,1H), 5.56 (dd,J=10, 9 Hz, 1H), 6.77 (m, 1H), 6.86 (m,1H), 7-29 (m,1H), 7.69 (d,J=8 Hz,2H), 7.75 (s,1H), 7.77 (s,1H), 7.87 (d,J=8 Hz,2H), 8.60 (s,1H).

HPLC Column Phenomenex Luna 3 μm, C8 4.6×150 mm.

Mobile phase $CH_3CN:H_2O:AcONH_4$=300:700:2.3; UV detection wavelength: 282 nm;

Flow rate: 1.0 mL/min.

Retention time (Compound (VII (a)))=8.6 min; retention time (Compound (VII (b)))=11.1 min.

From the results shown in FIG. 11 the deprotection reactions, which used trifluoroacetic acid as the first organic acid and anisole, thioanisole, acetonitrile and benzonitrile as carbocation scavengers, were found to be highly efficient reactions (reaction yields were 95% or greater).

In addition, FIG. 1 also shows the results obtained by the second aspect of the deprotection reaction according to the present invention. In the second aspect, the deprotection reaction was examined in a system in which the acid, specifically hydrochloric acid, which is a type of inorganic acid, was made available by the carbocation scavenger per se (30 equivalents based on the compound of Example 1) and methanol was used as solvent. From the results shown in FIG. 1, when using hydrochloric acid as the carbocation scavenger, and methanol, which is a non-halogen-based solvent, as reaction solvent, the deprotection reaction could be carried out without generating the amide compound.

Example 2

Lysine [(1R,2R)-2-(4-cyanophenyl)-1,3-thiazol-2-yl]-1-{2,4-difluorophenyl)-1-(1H-1,2,4-triazol-1-yl-methyl)propyl}-oxy] methyl dihydrogen phosphate ethanol (1/1/1)

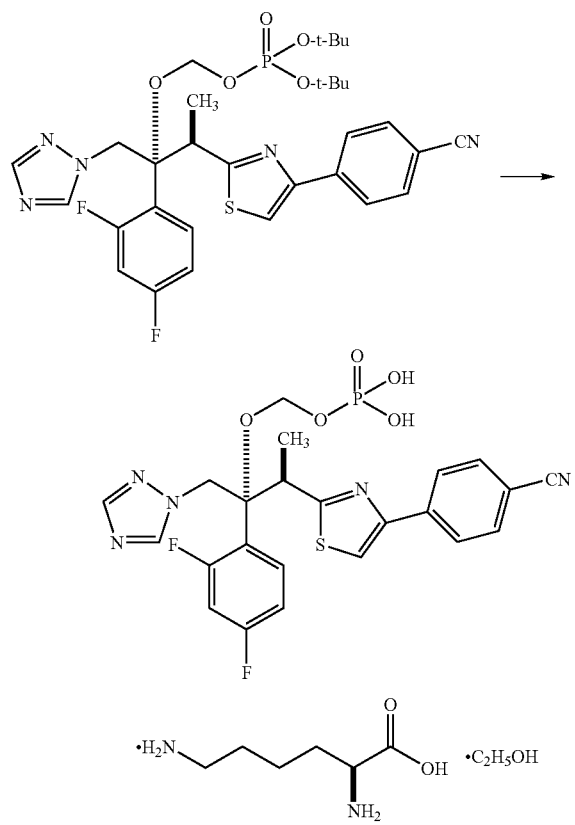

In 161 mL of methanol, 196 g of di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl phosphate crude product (0.15 mol) obtained in Example 1 was dissolved and cooled at a bath temperature of −20° C. Over 21 minutes, 250 mL of concentrated hydrochloric acid was added dropwise thereto, reaction was carried out at 0° C. for 4 hours. To the reaction solution was added a mixed solution of 264 g of $K_2HPO_4$ and 542 g of $Na_2HPO_4$ 12 hydrate dissolved in 1795 ml of aqueous solution and 700 mL of ethyl acetate. The upper layer was separated, washed with 1 L of 5% sodium chloride water, and then extracted with 10% $K_3PO_4$ water (1030 mL) twice separately. The $K_3PO_4$ extracted layer was transferred to a 3 L flask, 570 mL of butyl acetate was added thereto, and 210 mL of an aqueous solution of 5 N HCl was added dropwise under stirring. At this moment, the pH of the aqueous layer was 2.8. Next, the organic layer was washed with 570 mL of 5% sodium chloride water. A 89 mL aqueous solution in which 30.82 g of lysine had been dissolved was added, and the lower layer was fractionated. To the lysine water extracted layer was added 111 mL of ethanol and further added 41 mL of acetic acid. Furthermore, 337 mL of ethanol, 38 mL of water and 14 mL of acetic acid were added thereto, and the solution was transferred to a 3 L flask. Ethanol in the amount of 1345 mL was added thereto, 400 mg of seed crystal was also added, stirring was carried out for 6 hours at a bath temperature of 40° C. followed by stirring for 60 hours while leaving the bath temperature to 25° C., and the produced crystal was recovered by filtration. The crystal was washed with 160 mL of ethanol and dried for 2 hours at a bath temperature of 50° C. to obtain 64.5 g of the title compound as a yellowish white crystal (yield: 58%).

$^1$H-NMR ($D_2O$, 400 MHz) δ: 1.21 (t,J=7 Hz,3H), 1.26 (d,J=7 Hz,3H), 1.51 (m,2H), 1.75 (m,2H), 1.93 (m,2H), 3.05 (t,J=7 Hz,2H), 3.68 (q,J=7 Hz,2H), 3.78 (t, J=6 Hz, 1H), 3.85 (q,J=7 Hz,1H), 5.10 (d,J=16 Hz,1H), 5.17 (d,J=16 Hz,1H), 5.25 (dd,J=8,6 Hz,1H), 5.41 (dd,J=8.7 Hz,1H), 6.80 (m,1H), 6.83 (m,1H), 7.15 (m,1H), 7.57 (d,J=8 Hz,2H), 7.66 (s,1H), 7.71 (d,J=8 Hz,2H), 7.89 (s,1H), 8.70 (s,1H).

Example 3

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

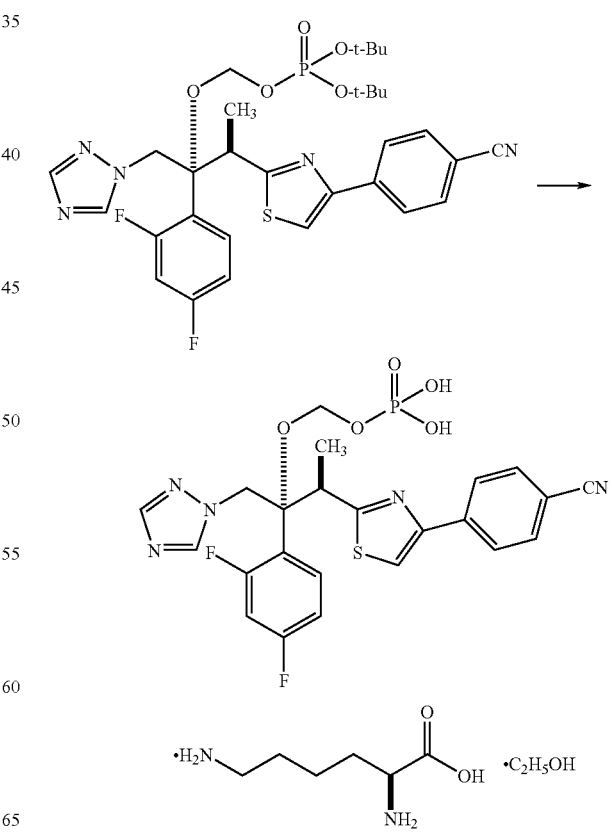

A crude product containing 131 g (0.20 mol) net of di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl phosphate synthesized similarly to Example 1 was dissolved by adding 90 mL of methanol and cooled at a bath temperature of −20° C. Over 90 minutes, 328 mL of concentrated hydrochloric acid was added dropwise thereto, reaction was carried out for two hours at 0° C. To the reaction solution was added a mixed solution of 347 g of $K_2HPO_4$ and 283 g of $Na_2HPO_4$ dissolved in 2620 mL of aqueous solution and 917 mL of ethyl acetate. The upper layer was separated, washed with 1.2 L of 5% sodium chloride water, and then extracted with 10% $K_3PO_4$ water (1356 mL) twice separately. The $K_3PO_4$ extracted layer was transferred to a 3 L flask, butyl acetate 757 mL was added, and 314 mL of an aqueous solution of 5N HCl was added dropwise thereto under stirring. At this moment, the pH of the aqueous layer was 2.2. Next, the organic layer was washed with 708 mL of 5% sodium chloride water. A 138 mL aqueous solution in which 45.4 g of lysine had been dissolved was added, and the lower layer was fractionated. To the lysine water extracted layer was added 166 mL of ethanol, and was further added 62 mL of acetic acid. Furthermore, 482 mL of ethanol, 50 mL of water and 18 mL of acetic acid were added thereto, and the solution was transferred to a 5 L flask. Ethanol in the amount of 1946 mL was added, 600 mg of seed crystal was added thereto, stirring was carried out for 6 hours at a bath temperature of 40° C. followed by stirring for 60 hours while leaving the bath temperature to 25° C., and the produced crystal was recovered by filtration. The crystal was washed with 240 mL of ethanol and dried for 2 hours at a bath temperature of 50° C. to obtain 100 g of the title compound (yield: 68%) as a faint yellowish white crystal. The obtained crystal was verified to be the same as in Example 2 by NMR data.

Example 4

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

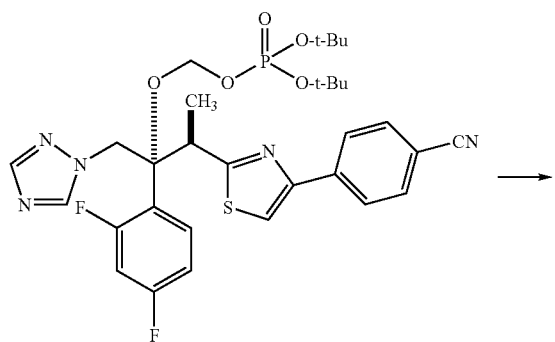

-continued

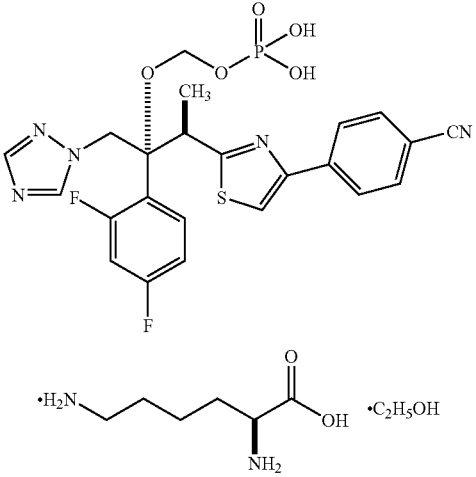

A crude product containing 126 g (0.19 mol) net of di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl phosphate synthesized similarly to Example 1 was dissolved by adding 267 mL of methanol and cooled at a bath temperature of −20° C. Over 15 minutes, 314 mL of concentrated hydrochloric acid was added dropwise thereto, reaction was carried out for two hours at 0° C. To the reaction solution was added a mixed solution of 332 g of $K_2HPO_4$ and 270 g of $Na_2HPO_4$ in 2514 mL of aqueous solution and 877 mL of ethyl acetate. The upper layer was separated, washed with 1.5 L of 5% sodium chloride water, and then extracted with 10% $K_3PO_4$ water (1316 mL) twice separately. The $K_3PO_4$ extracted layer was transferred to a 3 L flask 724 mL of butyl acetate was added thereto, and 316 mL of an aqueous solution of 5N HCl was added drop wise under stirring. At this moment, the pH of the aqueous layer was 1.9. Next, the organic layer was washed with 724 mL of 5% sodium chloride water. A 115 mL aqueous solution in which 39.4 g of lysine had been dissolved was added, and the lower layer was fractionated. To the lysine water extracted layer were added 62 mL of water and 192 mL of ethanol, and was further added 72 mL acetic acid. Ethanol in the amount of 2112 mL was added thereto, 560 mg of seed crystal was also added, stirring was carried out for 6 hours at a bath temperature of 40° C. followed by stirring for 60 hours while leaving the bath temperature to 25° C., and the produced crystal was recovered by filtration. The crystal was washed with 200 mL of ethanol and dried for 2 hours at a bath temperature of 50° C. to obtain 90.4 g of the title compound (yield: 64%) as a faint yellowish white crystal. The obtained crystal was verified to be the same as in Example 2 by NMR data.

Example 5

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

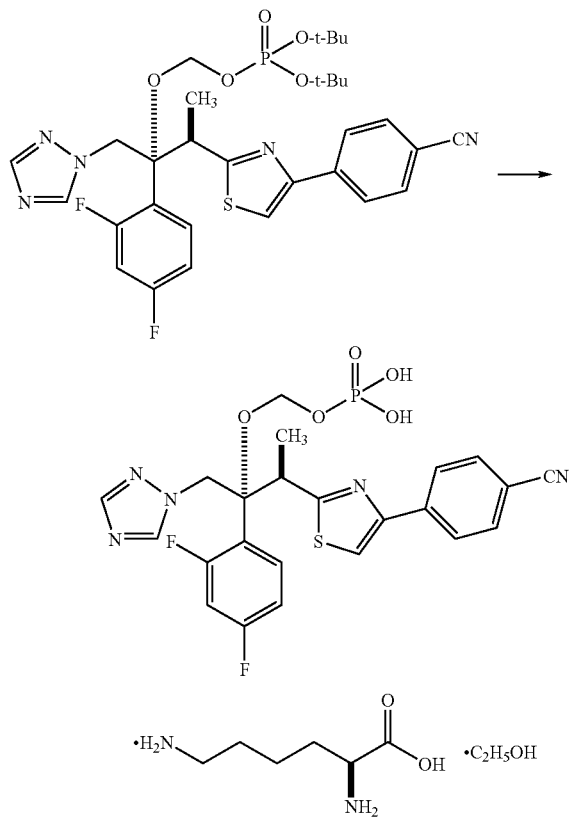

A crude product containing 126 g (0.19 mol) net of di-tert-butyl-{[(1R,2R)-2-(4-cyanophenyl)-1,3-thiazol-2-yl]-1-(2,4-difluorophenyl)-1-(1H-1,2,4-triazol-1-yl methyl)propyl}-oxy]methyl phosphate synthesized similarly to Example 1 was dissolved by adding 267 mL of methanol and cooled at a bath temperature of −20° C. Over 15 minutes, 314 mL of concentrated hydrochloric acid was added dropwise thereto, reaction was carried out for two hours at 0° C. To the reaction solution was added a mixed solution of 332 g of $K_2HPO_4$ and 270 g of $Na_2HPO_4$ in 2514 mL of aqueous solution and 877 mL of ethyl acetate. The upper layer was separated, washed with 1.5 L of 5% sodium chloride water, and then extracted with 10% $K_3PO_4$ water (1316 mL) twice separately. The $K_3PO_4$ extracted layer was transferred to a 3 L flask, 724 mL of butyl acetate was added thereto, and 276 mL of an aqueous solution of 5N HCl was added dropwise under stirring. At this moment, the pH of the aqueous layer was 2.5. Next, the organic layer was washed with 724 mL of 5% sodium chloride water. A 115 mL aqueous solution in which 39.4 g of lysine had been dissolved was added, and the lower layer was fractionated. To the lysine water extracted layer was added 62 mL of water and 192 mL of ethanol, and was also added 72 mL acetic acid. Ethanol in the amount of 2112 mL was added thereto, 50 mg of seed crystal was also added, stirring was carried out for 6 hours at a bath temperature of 40° C. followed by stirring for 60 hours while leaving the bath temperature to 25° C., and the produced crystal was recovered by filtration. The crystal was washed with 200 mL of ethanol and dried for 2 hours at a bath temperature of 50° C. to obtain 87.2 g of the title compound (yield: 62%) as a faint yellowish white crystal. The obtained crystal was verified to be the same as in Example 2 by NMR data.

Example 6

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

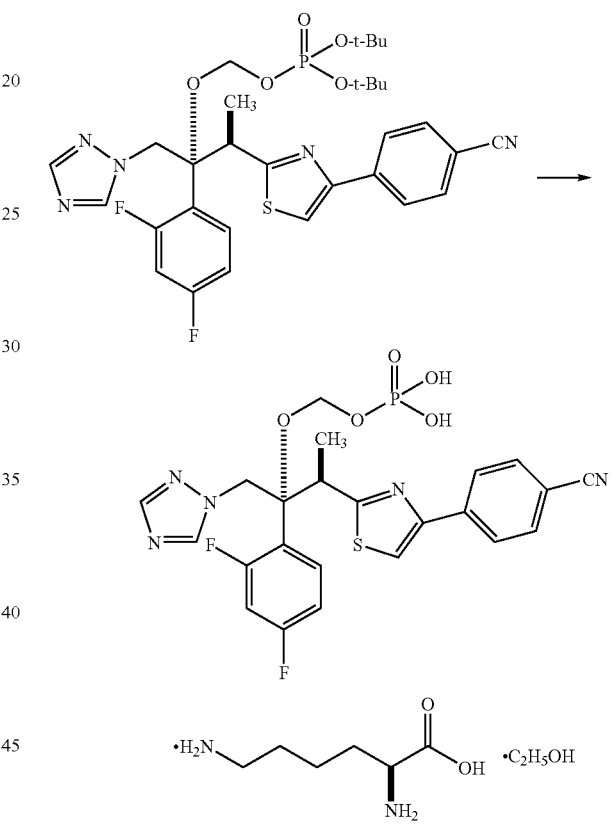

A crude product containing 96 g (0.14 mol) net of di-tert-butyl-{[(1R,2R)-2-(4-cyanophenyl)-1,3-thiazol-2-yl]-1-(2,4-difluorophenyl)-1-(1H-1,2,4-triazol-1-yl methyl)propyl}-oxy]methyl phosphate synthesized similarly to Example 1 was dissolved by adding 195 mL of methanol and cooled at a bath temperature of −20° C. Over 14 minutes, 334 mL of concentrated hydrochloric acid was added dropwise thereto, reaction was carried out for 5 hours at 0° C. To the reaction solution was added a mixed solution of 253 g of $K_2HPO_4$ and 206 g of $Na_2HPO_4$ in 1909 mL of aqueous solution and 660 mL of ethyl acetate. The upper layer was separated, washed with 1.2 L of 5% sodium chloride water, and then extracted with 10% $K_3PO_4$ water (1145 mL) twice separately. The $K_3PO_4$ extracted layer was transferred to a 3 L flask, 555 mL of butyl acetate was added thereto, and 227 mL of an aqueous solution of 5N HCl was added dropwise under stirring. At this moment, the pH of the aqueous layer was 2.2. Next, the organic layer was washed with 555 mL of 5% sodium chloride water. A 100 mL aqueous solution in which 35.4 g of lysine had been dissolved, 55 mL of ethanol and 278 mL of heptane were added thereto. To the aqueous layer obtained by fractionating the lower layer was added 95 mL of ethanol to obtain 313 g (A solution).

An amount of 78 g of A solution was weighed out, 11 mL of acetic acid, 9.1 mL of water and 343 mL of ethanol were added, 130 mg of seed crystal was added thereto, stirring was carried out for 40 minutes at 40° C. followed by stirring for 48 hours at 25° C. The produced crystal was then recovered by filtration. The crystal was washed with 50 mL of ethanol and dried for 2 hours at a bath temperature of 50° C. to obtain 17.4 g of the title compound (yield: 67%) as a faint yellowish white crystal. The obtained crystal was verified to be the same as in Example 2 by NMR data.

Example 7

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

An amount of 78 g of the A solution obtained in Example 6 was weighed out, 11 mL of acetic acid, 8.6 mL of water and 301 mL of ethanol were added thereto, 130 mg of seed crystal was further added, stirring was carried out for 40 minutes at 40° C. followed by stirring for 48 hours at 25° C. The produced crystal was then recovered by filtration. The crystal was washed with 50 mL of ethanol and dried for 2 hours at a bath temperature of 50° C. to obtain 18.7 g of the title compound (yield: 72%) as a faint yellowish white crystal. The obtained crystal was verified to be the same as in Example 2 by NMR data.

Example 8

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

An amount of 78 g of the A solution obtained in Example 6 was weighed out, 11 mL of acetic acid, 4.6 mL of water and 265 mL of ethanol were added thereto, 130 mg of seed crystal was further added, stirring was carried out for 40 minutes at 40° C. followed by stirring for 48 hours at 25° C. The produced crystal was then recovered by filtration. The crystal was washed with 50 mL of ethanol and dried for 2 hours at a bath temperature of 50° C. to obtain 17.3 g of the title compound (yield: 67%) as a faint yellowish white crystal. The obtained crystal was verified to be the same as in Example 2 by NMR data.

Example 9

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

An amount of 78 g of the A solution obtained in Example 6 was weighed out, 14.5 mL of acetic acid, 11.29 mL of water and 470 mL of ethanol were added thereto, 130 mg of seed crystal was further added, stirring was carried out for 40 minutes at 40° C. followed by stirring for 48 hours at 25° C. The produced crystal was then recovered by filtration. The crystal was washed with 50 mL of ethanol and dried for 2 hours at a bath temperature of 50° C. to obtain 19.4 g of the title compound (yield: 75%) as a faint yellowish white crystal. The obtained crystal was verified to be the same as in Example 2 by NMR data.

Example 10

Lysine [(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogen phosphate ethanol (1/1/1)

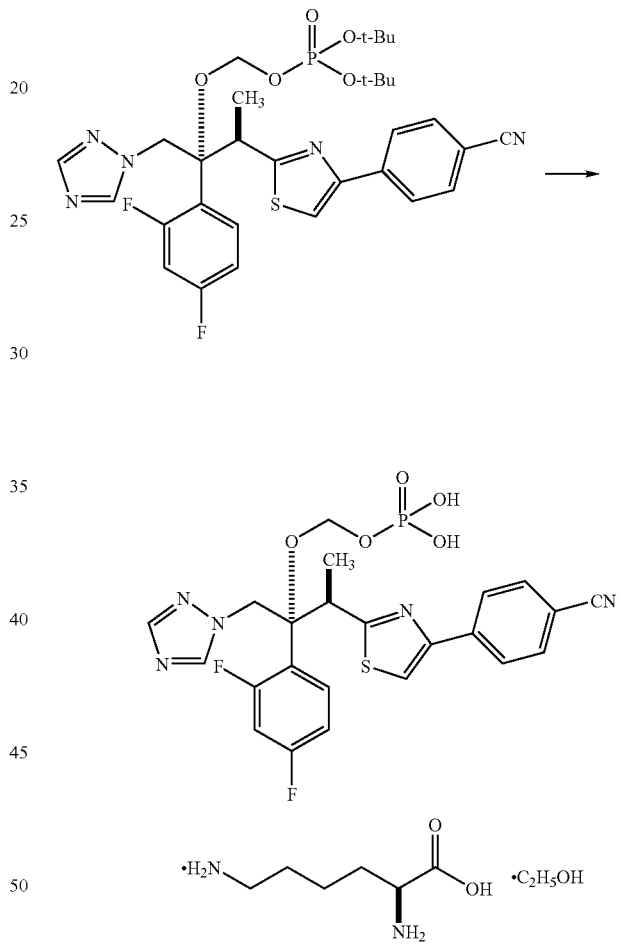

A crude product containing 124 g (0.19 mol) net of di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl phosphate synthesized similarly to Example 1 was dissolved by adding 175 mL of methanol and cooled at a bath temperature of −20° C. Over 15 minutes, 310 mL of concentrated hydrochloric acid was added dropwise thereto, reaction was carried out for 2 hours at 0° C. To the reaction solution was added a mixed solution of 329 g of $K_2HPO_4$ and 268 g of Na$_2$HPO$_4$ in 2356 mL of aqueous solution and 868 mL of ethyl acetate. The upper layer was separated, washed with 1.2 L of 5% sodium chloride water, and then extracted with 10% K$_3$PO$_4$ water (1300 mL) twice separately. The K$_3$PO$_4$ extracted layer was transferred to a 3 L flask, 707 mL of butyl acetate was added thereto, and 315 mL of an aqueous solution of 5N HCl was added dropwise under stirring. At this moment, the pH of the aqueous layer was 1.86. Next, the organic layer was washed with 672 mL of 5% sodium chloride water. A 153 mL aqueous solution in which 45 g of lysine had been dissolved and 76.5 mL of ethanol were added thereto, and the lower layer was fractionated. To the organic layer was added 25.5 mL of water, and the liquid fractionation procedure was carried out again. To the extracted aqueous layer were added 1620 mL of ethanol and 51 mL of acetic, 600 mg of seed crystal was added thereto followed by stirring for 60 hours while leaving the bath temperature to 25° C., and the produced crystal was recovered by filtration. The crystal was washed with 250 mL of ethanol and dried for 2 hours at a bath temperature of 50° C. to obtain 94.5 g of the title compound (yield: 68%) as a faint yellowish white crystal. The obtained crystal was verified to be the same as in Example 2 by NMR data.

Next, it will be illustrated that although Compound (IV) prepared according to the present invention is a mono lysine salt, it has excellent hygroscopicity in a comparison with a dilysine salt. Note that, a dilysine salt can be prepared by the methods disclosed in Published Japanese Translation of a PCT Application No. 2003-520235. While FIG. 2 (A) shows results of hygroscopicity of the mono lysine salt by the micro balance method, FIG. 2 (B) shows results of hygroscopicity of the dilysine salt by the micro balance method. From the results shown in FIG. 2, while moisture absorption phenomenon was observed at 50% RH with the dilysine salt, with the mono lysine salt, the moisture absorption phenomenon was observed at 70% RH. From these results, Compound (IV), which is a mono lysine salt was found to have improved hygroscopicity in a comparison with a dilysine salt. Note that, the measurement instrument used in the micro balance method was the following apparatus:

Gravimetric Vapour Sorption System (Model DVS-1 Surface Measurement System).

INDUSTRIAL APPLICABILITY

According to the preparation process of the present invention, without using the halogen-based on solvent, effective deprotection reaction of the tert-butyl phosphate intermediate compound can be realized, and can be applied to preparation of water-soluble azole prodrug at an industrial scale.

Description of Drawings

FIG. 1 shows the results according to the first and the second aspects of the deprotection reaction according to the present invention.

Figure 2A:
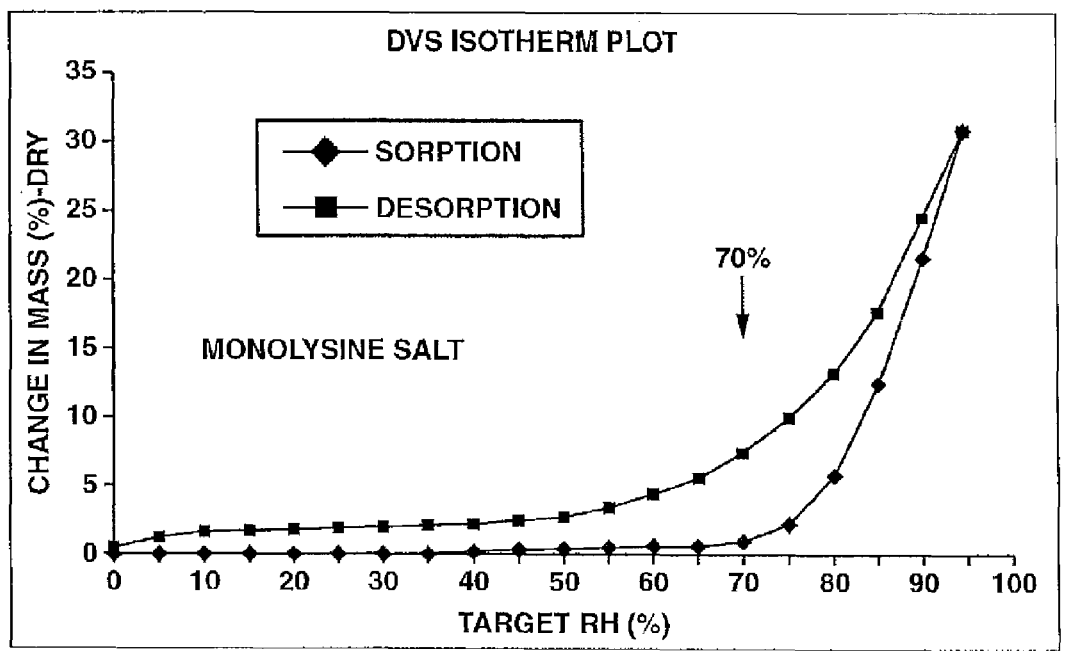
FIG. 2 (A) shows the results of hygroscopicity of the mono lysine salt by the micro balance method, and FIG. 2 (B) shows the results of hygroscopicity of the dilysine salt by the micro balance method Measurement of hygroscopicity of mono lysine salt was carried out at a temperature of 25.1° C., measurement of hygroscopicity of dilysine salt was carried out at 24.9° C.
Figure 2B:
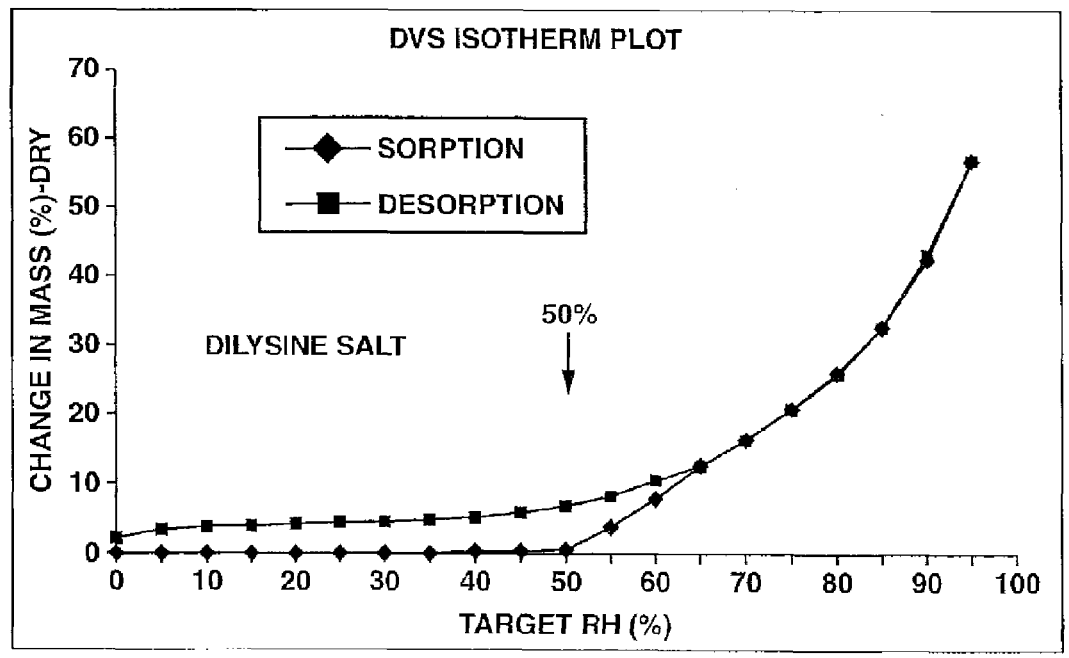

We claim:
1. A process for preparing a salt represented by Formula (I):

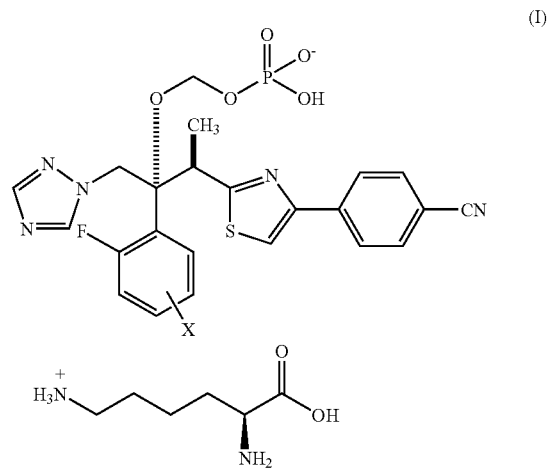

wherein X represents a fluorine atom bonded at position 4 or position 5 of a phenyl group, comprising the steps of:
(a) carrying out a deprotection reaction of a compound represented by Formula (II):

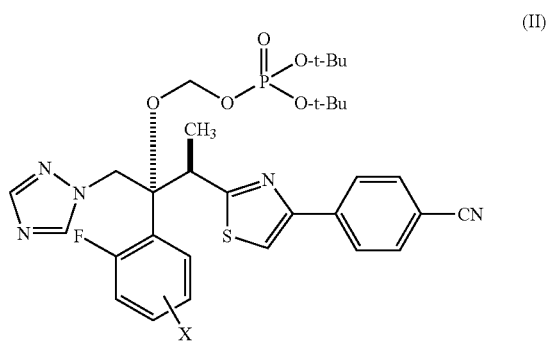

wherein X represents a fluorine atom bonded at position 4 or position 5 of a phenyl group,
(i) in the presence of a first organic acid and a carbocation scavenger or
(ii) in the presence of only a carbocation scavenger to produce a compound represented by Formula (III):

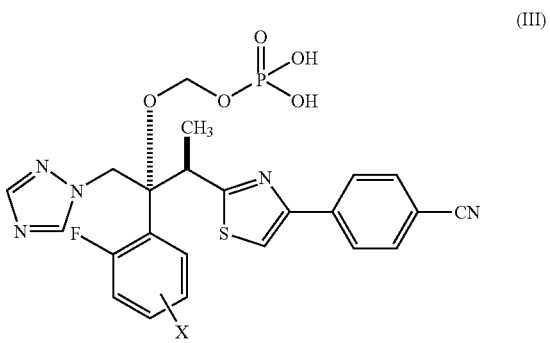

wherein X represents a fluorine atom bonded at position 4 or position 5 of a phenyl group; and
  (b) reacting the compound represented by Formula (III) with lysine in the presence of water, an organic solvent and an acid.

2. The process according to claim 1, wherein the first organic acid is selected from the group consisting of trifluoroacetic acid, methanesulfonic acid, trifluoromethane sulfonic acid, benzene sulfonic acid and toluene sulfonic acid.

3. The process according to claim 1, wherein the carbocation scavenger is selected from the group consisting of inorganic acid, C1-C6 alkoxybenzene which may have a substituent, C1-C6 alkylthiobenzene which may have a substituent, nitrile compound and mixtures thereof.

4. The process according to claim 3, wherein the inorganic acid is selected from the group consisting of hydrofluoric acid, hydrochloric acid, hydrobromic acid, hydroiodic acid, nitric acid, sulfuric acid and phosphoric acid.

5. The process according to claim 3, wherein the C1-C6 alkoxybenzene which may have a substituent is anisole or m-methoxy anisole.

6. The process according to claim 3, wherein the C1-C6 alkylthiobenzene is thioanisole.

7. The process according to claim 3, wherein the nitrile compound is selected from the group consisting of acetonitrile, propiononitrile and benzonitrile.

8. The process according to claim 1, wherein a solvent selected from the group consisting of ester solvent, ether solvent, alcohol solvent and mixed solvents thereof is used when the first organic acid and the carbocation scavenger is used in said step (a).

9. The process according to claim 1, wherein a solvent selected from the group consisting of ether solvent, alcohol solvent and mixed solvents thereof is used when only the carbocation scavenger is used in said step (a).

10. The process according to claim 8, wherein the ester solvent is selected from the group consisting of ethyl acetate, butyl acetate and mixed solvents thereof.

11. The process according to claim 8, wherein the ether solvent is selected from the group consisting of diethyl ether, dimethoxy ethane, methyl tert-butyl ether, tetrahydrofuran and mixed solvents thereof.

12. The process according to claim 8, wherein the alcohol solvent is selected from the group consisting of methanol, ethanol, 1-propanol, 2-propanol and mixed solvents thereof.

13. The process according to claim 9, wherein the carbocation scavenger is an inorganic acid.

14. The process according to claim 1, wherein the step (a) is carried out at a temperature of from −20° C. to 10° C.

15. The process according to claim 1, wherein the organic solvent is an organic solvent miscible with water, and the acid is a second organic acid.

16. The process according to claim 15, wherein the organic solvent miscible with water is selected from the group consisting of methanol, ethanol, 1-propanol, 2-propanol and mixed solvents thereof.

17. The process according to claim 15, wherein the organic solvent miscible with water is ethanol.

18. The process according to claim 15, wherein the second organic acid is selected from the group consisting of acetic acid, propionic acid and butyric acid.

19. The process according to claim 1, further comprising the steps of:
  (c) carrying out crystallization in the organic solvent miscible with water so as to produce a solvate of the salt represented by the Formula (I).

20. The process according to claim 19, wherein the solvate is a solvate represented by Formula (IV):

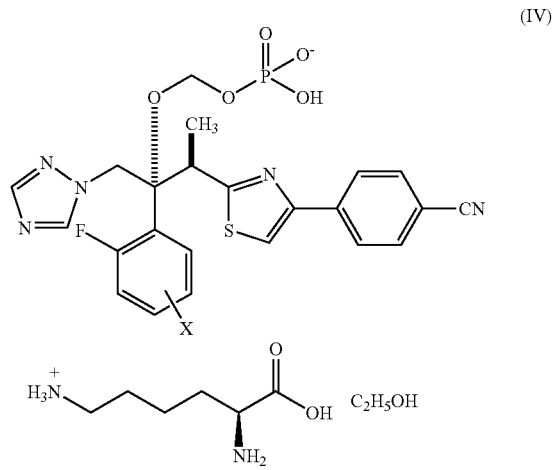

wherein X represents a fluorine atom bonded at position 4 or position 5 of a phenyl group, and the organic solvent miscible with water is ethanol.

21. The process according to claim 1, wherein the compound represented by the Formula (II) is obtained by reacting a compound represented by Formula (V):

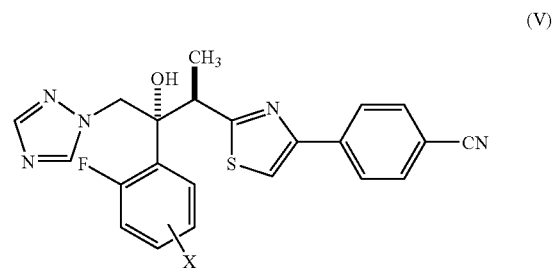

wherein X represents a fluorine atom bonded at position 4 or position 5 of a phenyl group, with a compound represented by Formula (VI):

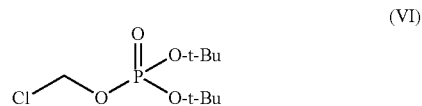

in a solvent containing a base.

22. The process of claim 1, wherein the deprotection reaction is carried out without the use of a halogen-based solvent.

23. The process of claim 1, wherein the deprotection reaction is carried out (i) in the presence of a first organic acid and a carbocation scavenger.

24. The process of claim 1, wherein the deprotection reaction is carried out (ii) in the presence of only a carbocation scavenger.

* * * * *